United States Patent [19]
Octavio et al.

[11] Patent Number: 6,025,535
[45] Date of Patent: *Feb. 15, 2000

[54] TOPSHEET FOR ABSORBENT ARTICLES EXHIBITING IMPROVED MASKING PROPERTIES

[75] Inventors: Maria Teresa Octavio, Caracas, Venezuela; James William Cree, Cincinnati, Ohio; Luis Eduardo Ravaglia, Raleigh, N.C.; Dennis Albert Thomas, Cincinnati, Ohio

[73] Assignee: The Procter & Gamble Company, Cincinnati, Ohio

[ * ] Notice: This patent issued on a continued prosecution application filed under 37 CFR 1.53(d), and is subject to the twenty year patent term provisions of 35 U.S.C. 154(a)(2).

[21] Appl. No.: 08/739,094

[22] Filed: Oct. 28, 1996

[51] Int. Cl.[7] .................................................. A61F 13/15
[52] U.S. Cl. ........................... 604/381; 604/382; 604/358
[58] Field of Search ..................... 604/358, 381, 604/382

[56] References Cited

U.S. PATENT DOCUMENTS

| | | |
|---|---|---|
| 3,952,745 | 4/1976 | Duncan . |
| 4,690,679 | 9/1987 | Mattingly, III et al. . |
| 4,710,186 | 12/1987 | DeRossett et al. . |
| 4,753,834 | 6/1988 | Braun et al. . |
| 4,798,757 | 1/1989 | Modrak et al. . |
| 4,801,494 | 1/1989 | Datta et al. . |
| 4,806,411 | 2/1989 | Mattingly, III et al. . |
| 4,868,031 | 9/1989 | Modrak et al. . |
| 5,006,394 | 4/1991 | Baird . |
| 5,219,341 | 6/1993 | Serviak et al. ........................... 604/361 |
| 5,261,899 | 11/1993 | Visscher et al. . |
| 5,281,378 | 1/1994 | Kozulla . |
| 5,318,735 | 6/1994 | Kozulla . |
| 5,342,336 | 8/1994 | Meirowitz et al. . |
| 5,431,643 | 7/1995 | Ouellette et al. . |
| 5,431,994 | 7/1995 | Kozulla . |
| 5,658,639 | 8/1997 | Curro et al. ............................. 604/381 |
| 5,670,110 | 9/1997 | Dirk et al. ............................... 264/504 |

FOREIGN PATENT DOCUMENTS

| | | |
|---|---|---|
| WO 93/19715 | 10/1993 | WIPO . |
| WO 95/23571 | 9/1995 | WIPO . |
| WO 96/00548 | 1/1996 | WIPO . |
| WO 96/00549 | 1/1996 | WIPO . |
| WO 97/10789 | 3/1997 | WIPO . |

*Primary Examiner*—John G. Weiss
*Assistant Examiner*—Dennis Ruhl
*Attorney, Agent, or Firm*—William Scott Andes; Caroline Wei-Berk; Mary Catherine Hentz

[57] ABSTRACT

The present invention provides a fluid previous fibrous, preferably nonwoven, web having a first surface and a second surface. The web comprises a hydrophilic nonwoven web comprising a plurality of individual, preferably whitened, brightened, and/or opacified, fibers associated with one another. The web includes a plurality of surface energy gradients defined by the boundaries of discontinuous, spaced regions of the web which are located on the first surface which exhibit a different surface energy than an adjacent portion of the web. The regions comprise depositions of a preferably whitened, brightened, and/or opacified low surface energy material randomly distributed over the first surface. In a preferred embodiment, the nonwoven web is formed of shaped fibers of substantially non-circular cross-section, preferably a trilobial or delta cross-section, which include whitening, brightening, and opacifying agents within the fiber material. Preferably, the low surface energy material includes whitening and opacifying agents within the material itself, with a preferred material comprising a UV curable silicone resin including a titanium dioxide particle suspension. The nonwoven fibrous webs of the present invention may be utilized advantageously as a topsheet and/or secondary topsheet in an absorbent article such as a diaper, sanitary napkin, or the like.

9 Claims, 3 Drawing Sheets

TOPSHEET FOR ABSORBENT ARTICLES EXHIBITING IMPROVED MASKING PROPERTIES

FIELD OF THE INVENTION

The present invention relates to fluid previous fibrous webs particularly suited for use as a topsheet or secondary topsheet in a disposable absorbent article, such as a diaper, sanitary napkin, panty liner, incontinence pad, or the like. The present invention further relates to such webs which exhibit improved masking and fluid handling properties for maintaining a clean and dry appearance under in-use conditions.

BACKGROUND OF THE INVENTION

All manner and variety of absorbent articles configured for the absorption of bodily fluids are, of course, well known. Current types of absorbent articles include sanitary napkins, pantiliners, disposable diapers, and incontinent articles.

One material which has been widely utilized as a topsheet material in absorbent articles is disclosed in commonly assigned U.S. Pat. No. 4,342,314 issued to Radel, et al. on Aug. 3, 1982 and hereby incorporated herein by reference. Radel, et al. discloses an absorbent bandage with a wearer-contacting topsheet comprising a resilient, macroscopically expanded, three-dimensional plastic web exhibiting a combination of fiber-like and plastic properties. In a preferred embodiment, the macroscopically expanded, three-dimensional, plastic web topsheet disclosed in Radel, et al. exhibits a fine scale three-dimensional microstructure comprising a regulated continuum of capillary networks originating in and extending from one surface of the web and terminating in the form of apertures in the opposite surface thereof to promote rapid fluid transport. The web's fiber-like appearance is comprised of a continuum of fiber-like elements, the opposed ends of each of the fiber-like elements are interconnected to at least one other of the fiber-like elements.

A typical capillary network in the Radel, et al. structure comprises an uppermost capillary opening or aperture formed by a multiplicity of fiber-like elements interconnected to one another in the uppermost plane of the web. Each of the fiber-like elements exhibits a substantially uniform U-shaped cross-section along its length. The cross-section of the fiber-like element comprises a base portion located in the wearer-contacting plane and a sidewall portion joined to each edge of the base portion, the sidewall portions extend generally in the direction of the absorbent pad-contacting surface of the web. The sidewall portions which intersect one another are joined to one another intermediate the wearing contacting surface and the absorbent pad contacting surface of the web, thereby forming a capillary network interconnecting the opposed surfaces of the web.

A topsheet of the type generally disclosed by Radel, et al. is highly effective in promoting rapid fluid transfer from the first, wearer-contacting surface to the second, absorbent pad-contacting surface of the topsheet. Accordingly, topsheets of this type have enjoyed widespread commercial success on catamenial pads due to their clean and dry appearance in use when contrasted to conventional nonwoven fibrous topsheets or two-dimensional films. While an absorbent article having a topsheet of the type disclosed in Radel, et al. is highly effective in promoting rapid transfer of bodily fluids from the first, wearer-contacting surface to the second, absorbent pad-contacting surface, the degree of masking of bodily fluids, e.g., menses, retained within the absorbent core is dependent upon the size of the capillary networks. As the size of the capillary networks decreases the amount of masking provided by the topsheet increases. However, if the capillary networks are too small bodily fluids are not able to pass through the topsheet into the absorbent core thereby exposing the skin to moisture.

Conventional nonwoven topsheets have been found to provide desirable visual and tactile properties from the wearer's perspective, as well as good flexibility and softness properties. However, the fluid-handling performance of conventional nonwoven topsheets has been found to be less than optimal, particularly with comparatively more viscous bodily fluids, contributing to a "wet" tactile impression after exposure to bodily fluids. In addition, residual fluid typically remaining within the nonwoven material itself after use creates a less-than-desirable visual impression.

With either conventional formed film topsheets or conventional nonwoven topsheets, one proposed solution to enhance the masking performance of such topsheets with regard to fluid within the absorbent article has been to employ opacifiers in the materials of the topsheet itself. For example, formed film topsheets and nonwoven topsheet materials have been developed which utilize whitening and/or opacifying agents such as titanium dioxide within the materials themselves. While such materials exhibit improved masking of underlying fluids below the topsheet, their light and often white coloration increases the visual contrast with residual bodily fluids remaining upon the surface after use, negating any improvement in masking of underlying fluids.

Accordingly, it would be desirable to provide a fluid previous web suitable for use as a topsheet in an absorbent article which provides the fluid handling capabilities of a formed film material and the softness of a nonwoven material.

It would also be desirable to provide a topsheet material having desirable visual and tactile properties, including masking and soft tactile impression, while providing good fluid handling performance.

SUMMARY OF THE INVENTION

The present invention provides a fluid previous fibrous, preferably nonwoven, web having a first surface and a second surface. The web comprises a hydrophilic nonwoven web comprising a plurality of individual, preferably whitened, brightened, and opacified, fibers associated with one another. The web includes a plurality of surface energy gradients defined by the boundaries of discontinuous, spaced regions of the web which are located on the first surface which exhibit a different surface energy than an adjacent portion of the web. The regions comprise depositions of a preferably whitened and opacified low surface energy material randomly distributed over the first surface.

In a preferred embodiment, the nonwoven web is formed of shaped fibers of substantially non-circular cross-section, preferably a trilobial or delta cross-section, which include whitening, brightening, and opacifying agents within the fiber material. Preferably, the low surface energy material includes whitening and opacifying agents within the material itself, with a preferred material comprising a UV curable silicone resin including a titanium dioxide particle suspension.

The nonwoven fibrous webs of the present invention may be utilized advantageously as a topsheet and/or secondary topsheet in an absorbent article such as a diaper, sanitary napkin, or the like.

BRIEF DESCRIPTION OF THE DRAWINGS

While the specification concludes with claims particularly pointing out and distinctly claiming the present invention, it is believed that the present invention will be better understood from the following description in conjunction with the accompanying drawings, in which like reference numbers identify like elements, and wherein:

DETAILED DESCRIPTION OF THE INVENTION

Figure 1:
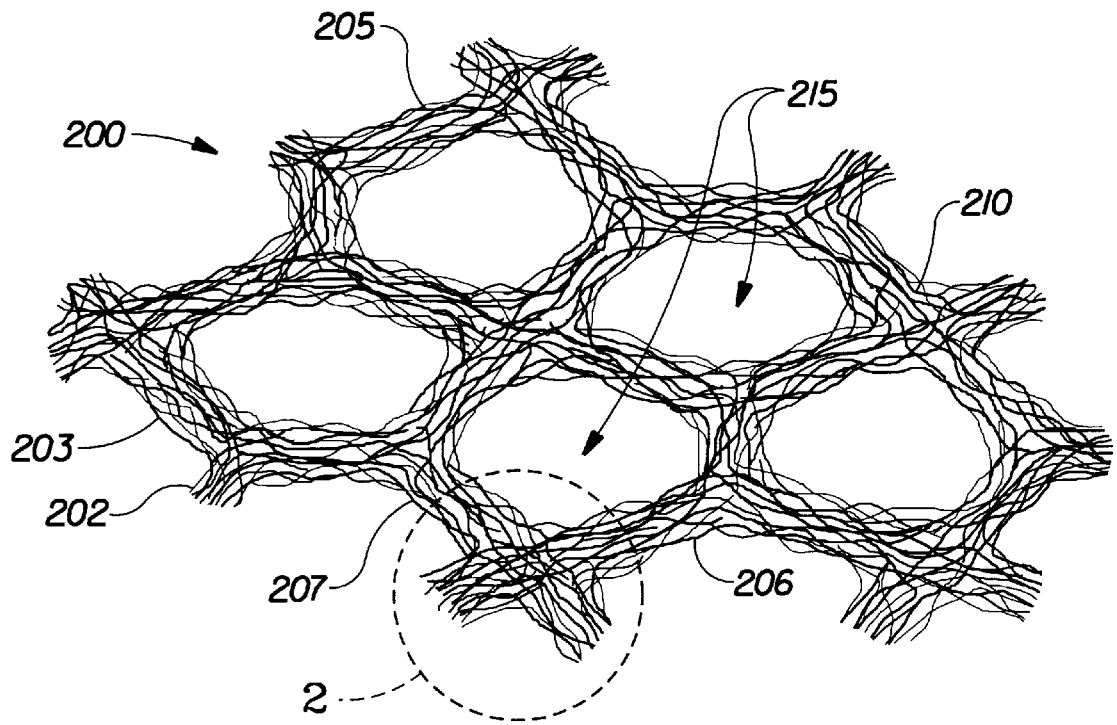
FIG. 1 is an enlarged, partially segmented, perspective illustration of a preferred fluid previous fibrous web according to the present invention.

FIG. 1 depicts a fluid-previous fibrous web 200 in accordance with the present invention. Fibrous web 200 preferably comprises a woven or nonwoven web formed of synthetic fibers (such as polypropylene, polyester, or polyethylene), natural fibers (such as wood, cotton, or rayon), or combinations of natural and synthetic fibers, as well as various paper, tissue, or paper-like fibrous materials. Nonwoven webs may be apertured by techniques known in the art such as needle punching, hydroentangling, ring-rolling, etc. Suitable nonwoven materials can be formed by various processes such as carding, spun-bonding, hydroentangling, and other processes familiar to those knowledgeable in the art of nonwovens. The fibers of the nonwoven material itself may be bonded to one another to provide integrity to the material by any of a number of suitable methods, including heat bonds, pressure bonds, ultrasonic bonds, dynamic mechanical bonds, or any other means known in the art.

Fibrous materials suitable for use in the present invention may either exhibit inherent porosity due to interfiber spacing and/or porosity due to formed apertures extending through the material. Porosity may be provided or enhanced by various mechanical means such as punching, slitting, severing, ring-rolling, hydroentangling, or any other suitable method.

Figure 2:
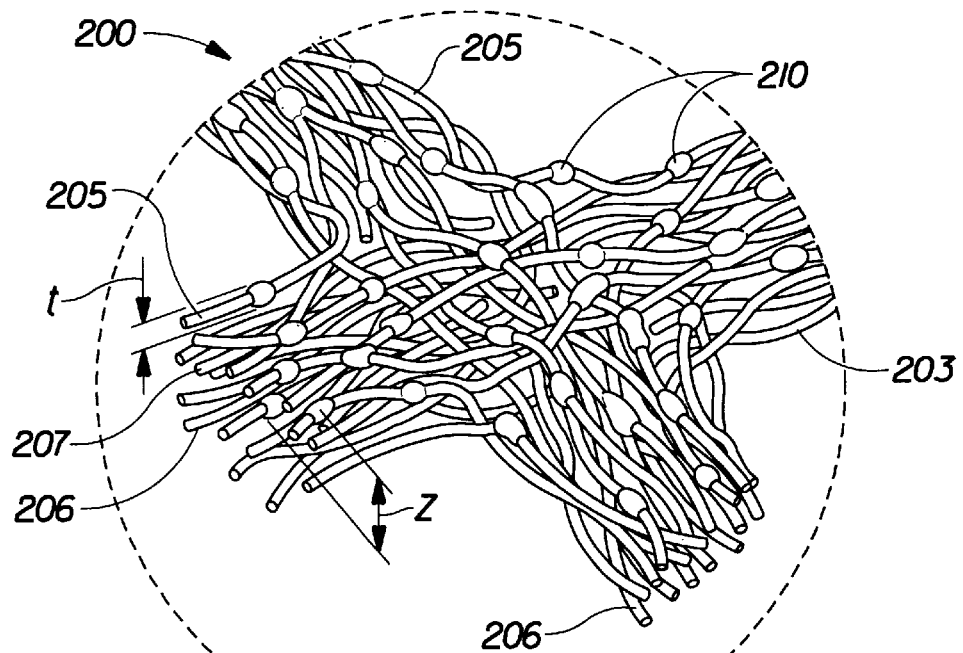
FIG. 2 is a further enlarged, partial view of the fibrous web of FIG. 1.

FIGS. 1 and 2 depict a fluid-previous fibrous web 200 in accordance with the present invention which is suitable for use as topsheet and/or secondary topsheet in an absorbent article such as a sanitary napkin. Fibrous web 200 includes a fluid-previous nonwoven web 202 which is preferably comprised of polypropylene fibers 203. Other suitable fibers include natural fibers such as wood, cotton, or rayon, or synthetic fibers such as polyester or polyethylene, bi-component fibers, or combinations of natural and synthetic fibers, as well as various paper, tissue, or paper-like fibrous materials.

The nonwoven web 202 has a first or upper surface 205 and a second surface or lower 206. The first surface 205 is spaced from the second surface 206 by an intermediate portion 207. The first surface 205 preferably has a plurality of regions 210 thereon which exhibit a comparatively low surface energy and preferably comprise a low surface energy surface treatment. A plurality of apertures 215 extend from the first surface 205 to the second surface 206 of the nonwoven web 202 depicted in FIG. 1.

Preferably, the regions 210 have a relatively low surface energy and a relatively low work of adhesion as compared to the fibers of the nonwoven which have a relatively high surface energy and a relatively high work of adhesion. Accordingly, the treated nonwoven web 200 exhibits a plurality of surface energy gradients defined by the boundaries of regions 210, i.e., the interfaces between regions 210 and the surrounding fiber surfaces, as will be discussed hereafter.

As depicted in FIG. 2, the relationship of the regions 210 to the surface topography (including individual fibers protruding upward from the upper surface of the web) is believed to be an important aspect of the present invention. Note the intermittent or discontinuous, spaced nature of the regions with regard to the surface direction of the web and the thickness direction of the web, particularly since the surface treatment as depicted in FIG. 2 is actually a plurality of discrete particles, droplets, or globules having a thickness dimension "t" which coat portions of individual fibers rather than a bridging or masking of the fibers which would occlude the interfiber pores. This discontinuity results in the generation of a plurality of small-scale surface energy gradients which are believed to be beneficial from a fluid-movement perspective. The theoretical background behind the performance of such small-scale surface energy gradients is discussed in greater detail in commonly-assigned, co-pending U.S. patent application Ser. No. 08/442,935, filed May 31, 1995 in the names of Ouellette, et al., the disclosure of which is hereby incorporated herein by reference.

Also clearly depicted in FIG. 2 is the penetration of the surface treatment into and below the first surface 205 of the nonwoven web 202, as indicated by the dimension "Z". While the majority of the regions 210 are concentrated near the first surface 205 itself, the treated regions extend downward through the web on a fiber-by-fiber basis to achieve a penetration analogous to that defined above with respect to the formed film web. Preferably, regions 210 are concentrated near the first surface 205 and decrease in frequency (increase in spacing) with increasing distance from the first surface, such that more low surface energy regions, and hence more surface energy gradients, are generated at or near the first surface 205 for greater effect on fluids on or near the first surface. On average, therefore, the upper regions of the web near the first surface would exhibit a lower average surface energy than that exhibited by lower regions of the web nearer to the second surface.

The nonwoven web 200 may be apertured by techniques known in the art such as needle punching, hydroentangling, ring-rolling (rolling between interengaged, corrugated rolls), slitting and tentering, embossing, etc. For configurations wherein the web has defined apertures, as shown in FIG. 1, the surface treatment 210 is preferably applied to the first surface of the nonwoven web after the aperturing operation is complete. Alternatively, the surface treatment 210 may be applied to the first surface of the nonwoven web prior to the aperturing operation.

Figure 3:
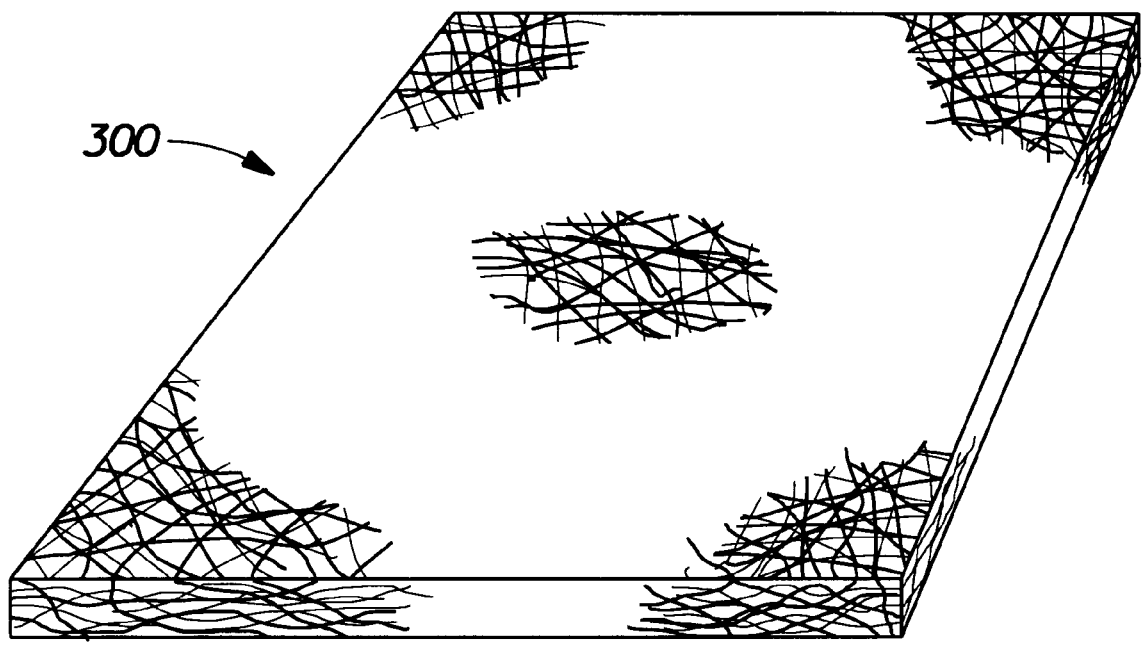
FIG. 3 is an enlarged, partially segmented, perspective illustration of another preferred fluid previous fibrous web according to the present invention.

In addition to apertured nonwoven structures having discrete apertures comparatively large in relation to the interfiber spacing, such as depicted in FIGS. 1 and 2, the principles of the present invention are believed to be applicable with equal effect to non-apertured nonwoven structures such as the nonwoven web 300 depicted in FIG. 3 having sufficient effective porosity to permit the desired fluid pass-through characteristics. This applicability is believed to be due to the non-occlusion of the interfiber capillaries (see FIG. 2) by the low surface energy treatment such that sufficient fluid passageways remain open for fluid transmission to the underlying structure. In a structure having discrete apertures comparatively large in relation to the interfiber spacing, non-occlusion is less important but still believed to be advantageous.

An example of a presently preferred non-apertured nonwoven fibrous material suitable for use in accordance with the present invention is a carded thermally-bonded nonwoven, having a basis weight of between about 18 and about 30 gsm, made with polypropylene fibers having a delta-shaped cross-section which are commercially available from Hercules, Inc. of Norcross, Ga., under the trade designation 11111-10A or 11111-10B. Another suitable material comprises a carded polypropylene staple fiber nonwoven having a basis weight of about 20 gsm which is commercially available from Fiberweb of Simpsonville, S.C., under the trade designation DFPN127. Other suitable fibrous materials include a spunbonded hydrophilic polypropylene nonwoven having a basis weight of about 23 gsm which is commercially available from Fiberweb of Simpsonville, S.C., under the trade designation CELESTRA®, and a synthetic carded nonwoven commercially available from Havix of Japan under the trade designation Havix S2146.

Although the foregoing discussion has focused on a true nonwoven substrate, it should be understood that the concepts of the present invention could be applied to woven or hybrid woven/nonwoven substrates in similar fashion. In doing so, recognition of the degree of porosity present in the interwoven structure is necessary to extrapolate the foregoing discussion regarding the porosity and interfiber capillary spacing of the nonwoven webs to interwoven structures.

The fluid-previous nonwoven webs according to the present invention have been found to exhibit a unique combination of properties viewed as important from a consumer perspective. More particularly, capillary webs according to the present invention have been found to exhibit good acquisition, dryness, and masking characteristics, which will be defined hereafter.

In general, acquisition is a reflection of the degree to which the fluid transport web does or does not interfere with fluid pass-through. Improved acquisition rates/times reflect little interference or impedance of fluid pass-through, as well as actual influence of fluid driving forces such as capillarity and surface energy gradients. Dryness is a reflection of the degree to which the fluid transport structure resists fluid transport in the opposite direction, in essence, the degree to which the structure acts as a one-way valve for fluid flow in a preferential direction. Masking reflects the cleanliness of the surface after fluid pass-through, further defined as the degree of coloration remaining (with a colored fluid) as well as the size or extend of the discolored region.

Typically, as surface energy of a given capillary web structure decreases uniformly the masking and dryness at the surface improve, but at the expense of a reduction in acquisition characteristics. Conversely, improvements in acquisition realized by a uniform increase in surface energy of a given capillary web structure are typically offset by reduced masking and dryness characteristics. By utilizing the surface energy gradient principles of the present invention, wherein the surface energy of the upper surface is decreased while the surface energy of the lower surface remains higher, and particularly with the preferred orientation and location of the gradients themselves, increases in acquisition, dryness, and/or masking characteristics may be obtained without sacrifices in the remaining parameters. Suitable analytical or test methods for determining web performance with regard to these attributes are described in greater detail in the ANALYTICAL METHODS section of aforementioned and incorporated Ouellette, et al. application.

A number of physical parameters should be considered in designing a web according to the present invention, more particularly with regard to appropriately sizing and positioning the surface energy gradients for proper fluid handling. Such factors include the magnitude of the surface energy differential (which depends upon the materials utilized), the application weight or quantity of low surface energy surface treatment (usually grams per square meter (gsm)), migratability of materials, bio-compatibility of materials, porosity or capillary size, overall web caliper and geometry, surface topography, fluid viscosity and surface tension, and the presence or absence of other structures on either side of the web.

Preferably, the regions 210 of the web 200 have a work of adhesion for water in the range of about 0 erg/cm$^2$ to about 150 erg/cm$^2$, more preferably in the range of about 0 erg/cm$^2$ to about 100 erg/cm$^2$, and most preferably in the range of about 0 erg/cm$^2$ to about 75 erg/cm$^2$. Preferably, the remainder of the web surrounding regions 210 has a work of adhesion for water in the range of about 0 erg/cm$^2$ to about 150 erg/cm$^2$, more preferably in the range of about 25 erg/cm$^2$ to about 150 erg/cm$^2$, and most preferably in the range of about 50 erg/cm$^2$ to about 150 erg/cm$^2$.

Preferably, the difference in the work of adhesion for water between the regions 210 and the remainder of the web is in the range of about 5 erg/cm$^2$ to about 145 erg/cm$^2$, more preferably in the range of about 25 erg/cm$^2$ to about 145 erg/cm$^2$, and most preferably in the range of about 50 erg/cm$^2$ to about 145 erg/cm$^2$.

The definition of "fiber", as utilized herein, is intended to also encompass a variety of fiber cross-sectional shapes besides the conventional round fibers such as is depicted in FIG. 2. As utilized herein, the term "shaped fiber" is intended to refer to fibers of substantially non-circular cross section. One such fiber is a type of fiber structure commonly referred to as a "capillary channel fiber", that is, a fiber having a capillary channel formed therein. Suitable fibers of this variety are described in greater detail in U.S. Pat. Nos. 5,200,248, 5,242,644, and 5,356,405, all of which issued to Thompson et al. on Apr. 6, 1993, Sep. 7, 1993, and Oct. 18, 1994, respectively, the disclosures of which are hereby incorporated herein by reference. Fibrous structures formed of such fibers may exhibit not only inter-fiber capillaries and spaces, but also intra-fiber capillary structures, and may be employed in various nonwoven structures such as carded and spunbonded nonwovens, either provided with discrete apertures or being generally non-apertured.

Figure 4:
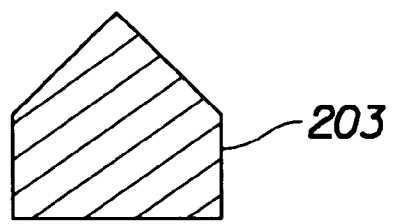
FIG. 4 is a cross-sectional view of a preferred type of fiber for use in nonwoven webs such as depicted in FIGS. 1 and 3.

FIG. 4 depicts a cross-sectional view of a particularly preferred shape of fiber 203 for use in a fibrous web suitable for use as a topsheet in accordance with the present invention. As shown in FIG. 4, the fiber 203 itself has a delta cross-section. Fibers having a delta cross-sectional shape such as is depicted in FIG. 4 are commercially available from Hercules of Norcross, Ga. under the trade designations 11111-10A and 11111-10B. These fibers, as well as suitable processes for making them, are described in greater detail in U.S. Pat. Nos. 5,281,378, 5,318,735, and 5,431,994, all assigned to Hercules, Inc. and issued to Kozulla on Jan. 25, 1994, Jun. 7, 1994, and Jul. 11, 1995, respectively, the disclosures of which are hereby incorporated herein by reference. Other references disclosing the use of shaped fibers include U.S. Pat. Nos. 4,798,757 and 4,868,031, both assigned to Hercules, Inc. and issued to Modrak et al. on Jan. 17, 1989 and Sep. 19, 1989, respectively, the disclosures of which are hereby incorporated herein by reference. The presently preferred delta-shaped fibers also include whitening, optically brightening, and opaciiying agents, as described below.

The use of shaped fibers such as the fiber depicted in FIG. 4 has been found to be advantageous from both a fluid handling and a masking perspective when utilized as a topsheet on an absorbent article. More particularly, without wishing to be bound by theory it is believed that when utilized as a substrate for the application of a low surface energy material to generate a plurality of small-scale surface energy gradients the shaped fibers enhance the ability of the surface energy gradients to impart motion to the fluid and to move it more quickly away from the upper, wearer-contacting surface. Moreover, the presence of angular fiber shapes is believed to impart additional reflectivity to the surface of the fibrous web. However, for some applications it may be desirable to employ non-shaped fibers of substantially circular cross-section, such as those commercially available from Hercules of Norcross, Ga. under the trade designation T-186.

To manufacture a web such as web 200 depicted in FIGS. 1 and 2 (or web 300 depicted in FIG. 3) having surface energy gradients according to the present invention, the nonwoven web is preferably formed by techniques known in the art and/or commercially obtained. The fibrous material may be intrinsically hydrophilic and/or may be rendered hydrophilic by techniques known in the art. A surface treatment having a relatively lower surface energy is then applied to the first surface of the web to form regions 210 and is preferably cured. A suitable surface treatment is a UV-curable silicone such as those commercially available from General Electric Company, Silicone Products Division, of Waterford, N.Y., under the designations UV 9300 and UV 9400, blended with a photocatalyst, such as one also commercially available from General Electric Company under the designation UV 9380C, in proportions by weight of 100 parts to 2.5 parts, respectively, and applied to the web at a rate of between about 1.5 and about 2.0 grams per square meter (gsm).

Surface treatments for generating regions 210 may be applied to the first surface 205 of the nonwoven web 202 by techniques known in the art such as screen printing, gravure printing, spraying, dip coating, etc. A presently preferred approach for applying surface treatments to a continuous web include application of the treatment via a smooth roll printing apparatus such that the resulting regions preferably exhibit a random, non-visually-discernible pattern (i.e., a pattern which is not visible to the normal naked eye when viewed at a distance of approximately 12 inches in a direction normal to the web surface). In addition, the regions 210 are preferably of a sufficiently fine scale that they may not be individually identifiable at a like distance, such that if the low surface energy material includes a colorant as described below the regions impart an overall visual property to the web in the aggregate rather than by providing a visually-discernible alternating color pattern.

When such a silicone blend is utilized on a nonwoven web such as depicted in FIGS. 1–3, coating application levels of about 1.5 to about 2.0 grams silicone per square meter of web surface area have performed satisfactorily, although other coating levels may prove suitable for certain applications depending upon the nature of the web material and surface, the characteristics of the fluid, etc.

Other suitable treatment materials include, but are not limited to, fluorinated materials such as fluoropolymers (e.g., polytetrafluoroethylene (PTFE), commercially available under the trade name TEFLON®) and chlorofluoropolymers. Other materials which may prove suitable for providing regions of reduced surface energy include Petrolatum, latexes, paraffins, and the like, although silicone materials are presently preferred for use in fluid-previous webs in the absorbent article context for their biocompatibility properties.

As used herein, the term "biocompatible" is used to refer to materials having a low level of specific adsorption for, or in other words a low affinity for, bio-species or biological materials such as gluco-proteins, blood platelets, and the like. As such, these materials tend to resist deposition of biological matter to a greater extent than other materials under in-use conditions. This property enables them to better retain their surface energy properties as needed for subsequent fluid handling situations. In the absence of biocompatibility, the deposition of such biological material tends to increase the roughness or non-uniformity of the surface, leading to increased drag force or resistance to fluid movement. Consequently, biocompatibility corresponds to reduced drag force or resistance to fluid movement, and hence faster access of fluid to the surface energy gradient and capillary structure. Maintenance of substantially the same surface energy also maintains the original surface energy differential for subsequent or enduring fluid depositions.

Biocompatibility, however, is not synonymous with low surface energy. Some materials, such as polyurethane, exhibit biocompatibility to some degree but also exhibit a comparatively high surface energy. Some low surface energy materials which might otherwise be attractive for use herein, such as polyethylene, lack biocompatibility. Presently preferred materials such as silicone and fluorinated materials advantageously exhibit both low surface energy and biocompatibility.

Suitable surfactants for hydrophilizing or increasing the surface energy of the selected regions of the web to have high surface energy include, for example, ethoxylated esters such as Pegosperse® 200-ML, manufactured by Glyco Chemical, Inc. of Greenwich, Conn., ATMER® 685, manufactured by ICI, glucose amides, tri-block copolymers of ethylene oxide and propylene oxide such as Pluronic® P103, manufactured by BASF, and copolymers of silicone and ethylene glycol such as DC190, manufactured by Dow Corning of Midland, Mich. Surfactants may be incorporated into the starting polymeric material (resin-incorporated surfactant (RIS)) of the web in accordance with the above-referenced and incorporated Published PCT Application WO 93/09741, or alternatively may be applied to the surface of the web by spraying, printing, or other suitable methods such as disclosed in U.S. Pat. No. 4,950,264, issued to Osborn on Aug. 21, 1990, the disclosure of which is hereby incorporated herein by reference.

In accordance with the present invention, the fibrous webs of FIGS. 1–3 are provided with additional whiteness, brightness, and/or opacity in addition to the surface energy gradients described above so as to enhance their masking performance in addition to their fluid handling capabilities. Whiteness, brightness, and/or opacity may be provided to such fibrous webs in combination with the surface energy gradients by various approaches, all of which are contemplated as being within the scope of the present invention.

The term "whiteness", as utilized herein, is intended to refer to the degree to which materials appear white in color when visually observed. "Whiteners" are therefore agents known in the art which are capable of imparting additional whiteness to materials to which they are added, incorporated, or applied. Whiteners are therefore a particular type of "colorant", utilized herein to describe agents known in the art which are capable of imparting additional coloration to materials to which they are added, incorporated, or applied. While other colors other than white may be desirable for certain applications, the color white is presently preferred for fibrous webs in accordance with the present invention because of the degree of cleanliness conveyed to consumers.

The term "brightness", as utilized herein, is intended to refer to the degree to which materials appear bright due to the reflectance of incident light when visually observed. "Brighteners" (also referred to as "optical brighteners") are therefore agents known in the art which are capable of imparting additional brightness to materials to which they are added, incorporated, or applied.

The term "opacity", as utilized herein, is intended to refer to the degree to which materials resist transmission therethrough of rays of light. "Opacifiers" are therefore agents known in the art which are capable of imparting additional opacity to materials to which they are added, incorporated, or applied.

In the context of the present invention, opacifiers increase the ability of the fibrous webs to obscure an observer's view of structures and bodily fluids contained within an absorbent article below the fibrous web. Colorants, particularly whiteners, provide a visually pleasing color to the fibrous web itself and may provide a camouflaging effect for any residue or residual fluid on the external surfaces of the fibrous web. Brighteners harness available light from the environment to reflect off of the surfaces of the fibrous web to enhance the lightness and cleanliness of its appearance after use.

Accordingly, fluid previous fibrous webs in accordance with the present invention include, in addition to the surface energy gradients described herein, at least one additional property selected from the list of colorants, optical brighteners, and opacifiers, and combinations thereof More preferably, fluid previous fibrous webs include at least two such additional properties. Most preferably, fluid previous fibrous webs include all three additional properties.

Such properties may be provided individually by individual elements, components, additives, materials, etc., or may be provided collectively by any one or more single materials. For example, $TiO_2$ (titanium dioxide) is one common material which functions both as a colorant (whitener) and an opacifier. Calcium carbonate ($CaCO_3$) is another suitable material for performing these functions.

In one approach in accordance with the present invention, whiteness, brightness, and/or opacity may be provided to the fibrous webs by the inclusion of opacifiers/colorants such as $TiO_2$ (titanium dioxide) and optical brighteners on or in the material of the fibers themselves. For example, the preferred polypropylene fibers from Hercules described above include both titanium dioxide and optical brighteners in the polypropylene resin to enhance the masking performance of the web by more thoroughly obscuring the user's view of colored fluids contained within and beneath the fibrous web and maintaining a bright, clean appearance of the fibrous web. Other alternative approaches would include the topical application of whiteners, brighteners, and/or opacifiers to the fibers either before or after their assemblage into the fibrous web by spraying, printing, or other suitable methods, either before, after, or during the application of the surface energy treatment.

The fluid handling properties of the surface energy treatment effectively minimize the residual fluid present on the surface of the web following use, thereby providing the maximum visibility for the fibers of the web. Accordingly, due to the minimization of the residual fluid the fibers may be whitened, brightened, and/or opacified to provide the desired degree of whiteness, brightness, and/or opacity without serving as a highlighted background for residual fluid.

Another approach to provide enhanced masking properties in accordance with the present invention is one in which the surface energy treatment preferably includes a coloring, brightening, and/or opacifying agent within the molecular structure of the material itself Accordingly, the regions 210 depicted in FIGS. 1 and 2 are preferably comprised of a colored, substantially-opaque low surface energy (hydrophobic) material. A particularly preferred color is white. Due to the hydrophobicity and biocompatibility of the material utilized for regions 210, the regions impart a clean, bright, substantially white appearance to the fibrous web 200 before, during, and after use.

Suitable materials for use in creating regions 210 include both low surface energy properties and whiteness, brightness, and/or opacity properties. One approach which has proven suitable is to provide a UV curable silicone polymer which incorporates a titanium dioxide particle suspension in the polymer. Such a surface treatment may be obtained by utilizing a proprietary silicone resin applied by Douglas-Hanson of Hammond, Wis., specifying UV Curable Blend Code #U2-5050W6, which exhibits both desirable whiteness and opacity properties. Other suitable approaches may include utilization of titanium dioxide, calcium carbonate, or other suitable whiteness/brightness/opacifying agents either suspended or bound within the molecular structure of the silicone (or other suitable low surface energy material such as those set forth in the listing above) and applied by the techniques described above, as well as the topical application of such agents to the regions after they are applied.

The use of an opaque, colored (preferably white) low surface energy treatment on the wearer-facing surface of a fibrous hydrophilic nonwoven web not only provides superior fluid handling properties due to the surface energy gradients provided by the treatment, but also superior masking performance due to the opacity and whiteness provided by the treatment. The effectiveness of the surface energy gradients in driving fluid, particularly residual fluid, from the surface of the nonwoven material maximizes the effectiveness of the opacity and whiteness of the small, preferably randomly-placed and non-visually-discernible, regions in providing an overall clean and dry appearance to the web.

In yet another approach in accordance with the present invention, a synergistic effect in terms of improved fluid handling and masking characteristics has been observed with the combined utilization of whitened, brightened, and/or opacified fibers and whitened, brightened, and/or opacified low surface energy materials, particularly with the use of shaped fibers. The fluid handling properties imparted by the surface energy gradients effectively minimize the presence of residual fluid on the surface of the web to provide the fibers and surface energy treatment with the maximum degree of visibility such that their whiteness and opacity properties may be best appreciated by the wearer. Moreover, the use of shaped fibers in such a fibrous web is particularly preferred for the additional benefits provided by such fibers, as described above.

Representative Absorbent Article

As used herein, the term "absorbent article" refers to devices which absorb and contain body exudates, and, more specifically, refers to devices which are placed against or in proximity to the body of the wearer to absorb and contain the various exudates discharged from the body. The term "disposable" is used herein to describe absorbent articles which are not intended to be laundered or otherwise restored or reused as an absorbent article (i.e., they are intended to be discarded after a single use, and, preferably, to be recycled, composted or otherwise disposed of in an environmentally compatible manner). A "unitary" absorbent article refers to absorbent articles which are formed of separate parts united together to form a coordinated entity so that they do not require separate manipulative parts like a separate holder and pad.

Figure 5:
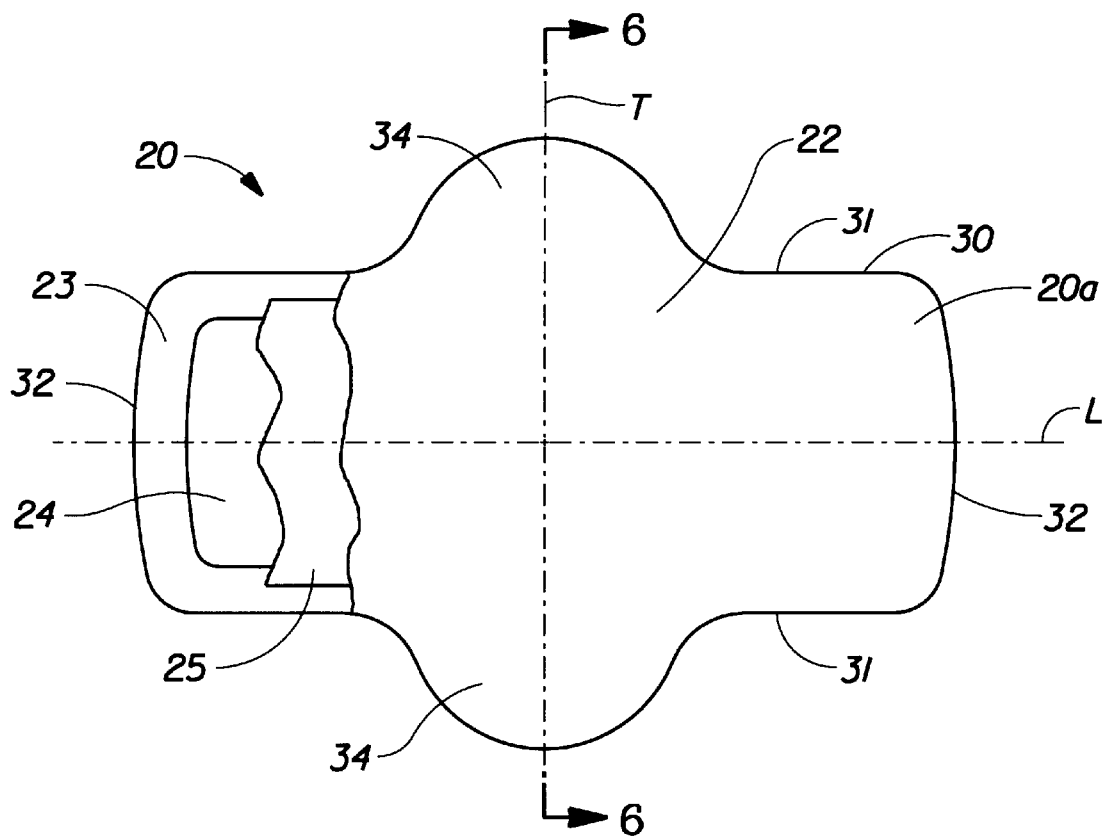
FIG. 5 is a top plan view of an absorbent article in the form of a sanitary napkin with portions cut-away to more clearly show the construction of the sanitary napkin.

A representative embodiment of a unitary disposable absorbent article utilizing a fluid previous web of the present invention is the catamenial pad, sanitary napkin 20, shown in FIG. 5. As used herein, the term "sanitary napkin" refers to an absorbent article which is worn by females adjacent to the pudendal region, generally external to the urogenital region, and which is intended to absorb and contain menstrual fluids and other vaginal discharges from the wearer's body (e.g., blood, menses, and urine). Interlabial devices which reside partially within and partially external of the wearer's vestibule are also within the scope of this invention. As used herein, the term "pudendal" refers to the externally visible female genitalia. It should be understood, however, that the present invention is also applicable to other feminine hygiene or catamenial pads such as pantiliners, or other absorbent articles such as diapers, incontinence briefs, and the like.

FIG. 5 is a plan view of the sanitary napkin 20 in its flat-out state with portions of the structure being cut-away to more clearly show the construction of the sanitary napkin 20 and with the portion of the sanitary napkin 20 which faces or contacts the wearer, oriented towards the viewer. As shown in FIG. 5, the sanitary napkin 20 preferably comprises a topsheet 22 having a first or body facing surface 22a and a second or garment facing surface 22b, a fluid impervious backsheet 23 joined with topsheet 22, and an absorbent core 24 positioned between the topsheet 22 and the backsheet 23.

The sanitary napkin 20 has two surfaces, a body-contacting surface or body facing surface 20a and a garment facing surface 20b. The sanitary napkin 20 is shown in FIG. 5 as viewed from its body facing surface 20a. The body facing surface 20a is intended to be worn adjacent to the body of the wearer while the garment facing surface 20b is on the opposite side and is intended to be placed adjacent to the wearer's undergarments or clothing when the sanitary napkin 20 is worn. The sanitary napkin 20 has two centerlines, a longitudinal centerline "L" and a transverse centerline "T". The term "longitudinal", as used herein, refers to a line, axis or direction in the plane of the sanitary napkin 20 that is generally aligned with (e.g., approximately parallel to) a vertical plane which bisects a standing wearer into left and right body halves when the sanitary napkin 20 is worn. The terms "transverse" or "lateral" as used herein, are interchangeable, and refer to a line, axis or direction which lies within the plane of the sanitary napkin 20 that is generally perpendicular to the longitudinal direction. FIG. 5 also shows that the sanitary napkin 20 has a periphery 30 which is defined by the outer edges of the sanitary napkin 20 in which the longitudinal edges (or "side edges") are designated 31 and the end edges (or "ends") are designated 32.

Figure 6:
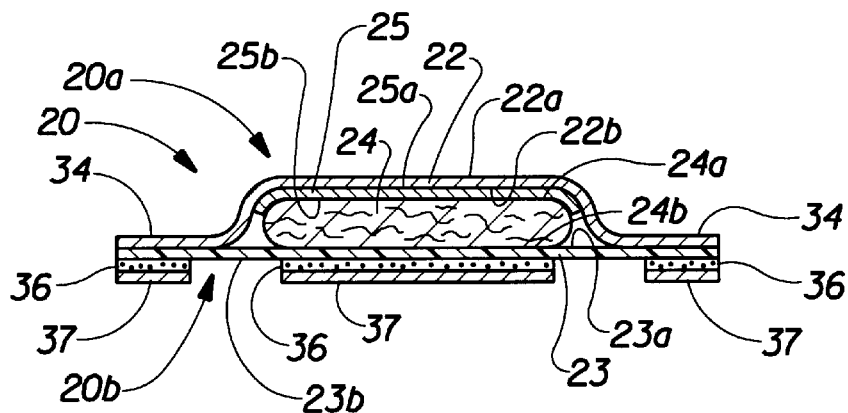
FIG. 6 is a cross-sectional view of the sanitary napkin of FIG. 5 taken along the section line 6—6.

FIG. 5 shows a preferred embodiment of the sanitary napkin 20 in which the topsheet 22 and the backsheet 23 have length and width dimensions generally larger than those of the absorbent core 24. The topsheet 22 and the backsheet 23 extend beyond the edges of the absorbent core 24 to thereby form not only portions of the periphery but also side flaps 34. As shown in FIGS. 5 and 6, the sanitary napkin 20 may also include a secondary topsheet 25 located between the topsheet 22 and the upper surface 24a of the absorbent core 24.

Sanitary napkin 20 preferably includes optional side flaps or "wings" 34 that are folded around the crotch portion of the wearer's panties. The side flaps 34 can serve a number of purposes, including, but not limited to protecting the wearer's panties from soiling and keeping the sanitary napkin secured to the wearer's panties.

FIG. 6 is a cross-sectional view of the sanitary napkin 20 taken along transverse section line 6—6 of FIG. 5. As can be seen in FIG. 6, the sanitary napkin 20 preferably includes an adhesive fastening means 36 for attaching the sanitary napkin 20 to the undergarment of the wearer. Removable release liners 37 cover the adhesive fastening means 36 to keep the adhesive from sticking to a surface other than a crotch portion of the undergarment prior to use or experiencing contamination and degradation.

The sanitary napkin 20 can be of any thickness, including relatively thick or relatively thin. The embodiment of the sanitary napkin 20 shown in FIGS. 5 and 6 is intended to be an example of a relatively thin sanitary napkin. It should be understood, however, when viewing these figures that the number of layers of material shown tends to cause the sanitary napkin to appear much thicker than it actually is. A "thin" sanitary napkin 20 preferably has a caliper of less than about 3 millimeters. The thin sanitary napkin 20 shown should also be relatively flexible, so that it is comfortable for the wearer.

Optionally, the sanitary napkin may be extensible or stretchable. Examples of extensible or stretchable sanitary napkins are disclosed in commonly-assigned, copending U.S. patent applications Ser. No. 07/915,133, filed Jul. 23, 1992 in the names of Osborn, et al., and Ser. No. 07/913,204, filed Jul. 23, 1992 in the names of Osborn, et al., the disclosures of which are hereby incorporated herein by reference.

In use, the sanitary napkin 20 can be held in place by any support means or attachment means well-known for such purposes. Preferably, the sanitary napkin is placed in the user's undergarment or panty and secured thereto by a fastener such as an adhesive 36. The adhesive 36 provides a means for securing the sanitary napkin 20 in the crotch portion of the panty. Thus, a portion or all of the outer surface of the backsheet 23 is coated with adhesive. Any adhesive or glue used in the art for such purposes can be used for the adhesive herein, with pressure-sensitive adhesives being preferred. Suitable adhesives are manufactured by H. B. Fuller Company of St. Paul, Minn., under the designation HL-2238. Suitable adhesive fasteners are also described in U.S. Pat. No. 4,917,697. Before the sanitary napkin is placed in use, the pressure-sensitive adhesive 36 is typically covered with a removable release liner 37 in order to keep the adhesive 36 from drying out or adhering to a surface other than the crotch portion of the panty prior to use. Suitable release liners 37 are also described in the above-referenced U.S. Pat. No. 4,917,697. Any commercially available release liners commonly used for such purposes can be utilized herein. A non-limiting example of a suitable release liner is BL30MG-A Silox 4P/O, which is manufactured by the Akrosil Corporation of Menasha, Wis. The sanitary napkin 20 of the present invention is used by removing the release liner 37 and thereafter placing the sanitary napkin 20 in a panty so that the adhesive 36 contacts the panty. The adhesive 36 maintains the sanitary napkin in its position within the panty during use.

In a preferred embodiment, the sanitary napkin 20 has two flaps 34 each of which are adjacent to and extend laterally from the side edge of the absorbent core. The flaps 34 are configured to drape over the edges of the wearer's panties in the crotch region so that the flaps are disposed between the edges of the wearer's panties and the thighs. The flaps 34 serve at least two purposes. First, the flaps 34 help serve to prevent soiling of the wearer's body and panties by menstrual fluid, preferably by forming a double wall barrier along the edges of the panty. Second, the flaps 34 are preferably provided with attachment means on their garment surface so that the flaps can be folded back under the panty and attached to the garment facing side of the panty. In this way, the flaps 34 serve to keep the sanitary napkin 20 properly positioned in the panty. The flaps 34 can be constructed of various materials including materials similar to the topsheet, backsheet, tissue, or combination of these materials. Further, the flaps 34 may be a separate element attached to the main body of the napkin or can comprise extensions of the topsheet and backsheet (i.e., unitary). A number of sanitary napkins having flaps suitable or adaptable for use with the sanitary napkins of the present invention are disclosed in U.S. Pat. No. 4,687,478 issued to Van Tilburg on Aug. 18, 1987; U.S. Pat. No. 4,589,876 issued to Van Tilburg on May 20, 1986; and U.S. Pat. No. 4,608,047 issued to Mattingly on Aug. 26, 1986. Each of these patents are incorporated herein by reference.

The absorbent core 24 may be any absorbent means which is capable of absorbing or retaining liquids (e.g., menses and/or urine). As shown in FIG. 5, the absorbent core 24 has a body facing surface, a garment facing surface, side edges, and end edges. The absorbent core 24 may be manufactured in a wide variety of sizes and shapes (e.g., rectangular, oval, hourglass, dog bone, asymmetric, etc.) and from a wide variety of liquid-absorbent materials commonly used in sanitary napkins and other absorbent articles such as comminuted wood pulp which is generally referred to as airfelt. Examples of other suitable absorbent materials include creped cellulose wadding; meltblown polymers including coform; chemically stiffened, modified or cross-linked cellulosic fibers; synthetic fibers such as crimped polyester fibers; peat moss; tissue including tissue wraps and tissue laminates; absorbent foams; absorbent sponges; superabsorbent polymers; absorbent gelling materials; or any equivalent material or combinations of materials, or mixtures of these.

The configuration and construction of the absorbent core may also be varied (e.g., the absorbent core 24 may have varying caliper zones (e.g., profiled so as to be thicker in the center), hydrophilic gradients, superabsorbent gradients, or lower density and lower average basis weight acquisition zones; or may comprise one or more layers or structures). The total absorbent capacity of the absorbent core 24 should, however, be compatible with the design loading and the intended use of the sanitary napkin 20. Further, the size and absorbent capacity of the absorbent core may be varied to accommodate different uses such as incontinence pads, pantiliners, regular sanitary napkins, or overnight sanitary napkins. In addition, the absorbent core 24 may be comprised of certain materials or configurations to provide flexibility, if so desired.

Exemplary absorbent structures for use as the absorbent core 24 of the present invention are described in U.S. Pat. No. 4,950,264 issued to Osborn on Aug. 21, 1990; U.S. Pat. No. 4,610,678 issued to Weisman et al. on Sep. 9, 1986; U.S. Pat. No. 4,834,735 issued to Alemany et al. on May 30, 1989; and European Patent Application No. 0 198 683, The Procter & Gamble Company, published Oct. 22, 1986 in the name of Duenk, et al. Each of these patents are incorporated herein by reference.

The backsheet 23 and the topsheet 22 are positioned adjacent the garment facing surface and the body facing surface, respectively, of the absorbent core 24 and are preferably joined thereto and to each other by attachment means (not shown) such as those well known in the art. For example, the backsheet 23 and/or the topsheet 22 may be secured to the absorbent core 24 or to each other by a uniform continuous layer of adhesive, a patterned layer of adhesive, or an array of separate lines, spirals, or spots of adhesive. Adhesives which have been found to be satisfactory are manufactured by H. B. Fuller Company of St. Paul, Minn., under the designation HL-1258, and by Findley of Minneapolis, Minn., under the designation H-2031. The attachment means will preferably comprise an open pattern network of filaments of adhesive as is disclosed in U.S. Pat. No. 4,573,986 issued to Minetola, et al. on Mar. 4, 1986, and which is incorporated herein by reference. An exemplary attachment means of an open pattern network of filaments comprises several lines of adhesive filaments swirled into a spiral pattern such as illustrated by the apparatus and method shown in U.S. Pat. No. 3,911,173 issued to Sprague, Jr. on Oct. 7, 1975; U.S. Pat. No. 4,785,996 issued to Zieker, et al. on Nov. 22, 1978; and U.S. Pat. No. 4,842,666 issued to Werenicz on Jun. 27, 1989. Each of these patents are incorporated herein by reference. Alternatively, the attachment means may comprise heat bonds, pressure bonds, ultrasonic bonds, dynamic mechanical bonds, or any other suitable attachment means or combinations of these attachment means as are known in the art.

The backsheet 23 has a body facing surface and a garment facing surface. The backsheet 23 is impervious to liquids (e.g., menses and/or urine) and is preferably manufactured from a thin plastic film, although other flexible liquid impervious materials may also be used. As used herein, the term "flexible" refers to materials which are compliant and will readily conform to the general shape and contours of the human body. The backsheet 23 prevents the exudates absorbed and contained in the absorbent core 24 from wetting articles which contact the sanitary napkin 20 such as pants, pajamas and undergarments. The backsheet 23 may thus comprise a woven or nonwoven material, polymeric films such as thermoplastic films of polyethylene or polypropylene, or composite materials such as a film-coated nonwoven material. Preferably, the backsheet is a polyethylene film having a thickness of from about 0.012 mm (0.5 mil) to about 0.051 mm (2.0 mils). Exemplary polyethylene films are manufactured by Clopay Corporation of Cincinnati, Ohio, under the designation P18-1401 and by Tredegar Film Products of Terre Haute, Ind., under the designation XP-9818. The backsheet is preferably embossed and/or matte finished to provide a more clothlike appearance. Further, the backsheet 23 may permit vapors to escape from the absorbent core 24 (i.e., breathable) while still preventing exudates from passing through the backsheet 23.

The topsheet 22 is compliant, soft feeling, and non-irritating to the wearer's skin. Further, the topsheet 22 is liquid previous permitting liquids (e.g., menses and/or urine) to readily penetrate through its thickness. A suitable topsheet 22 may be manufactured from a wide range of materials such as woven and nonwoven materials; polymeric materials such as apertured formed thermoplastic films, apertured plastic films, and hydroformed thermoplastic films; porous foams; reticulated foams; reticulated thermoplastic films; and thermoplastic scrims. Suitable woven and nonwoven materials can be comprised of natural fibers (e.g., wood or cotton fibers), synthetic fibers (e.g., polymeric fibers such as polyester, polypropylene, or polyethylene fibers) or from a combination of natural and synthetic fibers. In a preferred embodiment, the topsheet 22 comprises a fibrous web in accordance with the present invention as described above.

Where a secondary topsheet 25 comprising a fibrous web in accordance with the present invention is employed, other materials such as an apertured formed film of a polymeric film material, such as polyethylene, polypropylene, or other suitable material, may be utilized as a topsheet 22. The same holds true for secondary topsheet 25 if the topsheet 22 comprises a fibrous web in accordance with the present invention. Suitable formed films are described in U.S. Pat. No. 3,929,135, entitled "Absorptive Structures Having Tapered Capillaries", which issued to Thompson on Dec. 30, 1975; U.S. Pat. No. 4,324,246 entitled "Disposable Absorbent Article Having A Stain Resistant Topsheet", which issued to Mullane, et al. on Apr. 13, 1982; U.S. Pat. No. 4,342,314 entitled "Resilient Plastic Web Exhibiting Fiber-Like Properties", which issued to Radel. et al. on Aug. 3, 1982; U.S. Pat. No. 4,463,045 entitled "Macroscopically Expanded Three-Dimensional Plastic Web Exhibiting Non-Glossy Visible Surface and Cloth-Like Tactile Impression", which issued to Ahr et al. on Jul. 31, 1984; and U.S. Pat. No. 5,006,394 "Multilayer Polymeric Film" issued to Baird on Apr. 9, 1991. Each of these patents are incorporated herein by reference. One suitable topsheet for the present invention is the formed film described in one or more of the above patents and marketed on sanitary napkins by The Procter & Gamble Company of Cincinnati, Ohio as "DRI-WEAVE".

Such a polymeric film topsheet may optionally be comprised of a multilayer polymeric film which exhibits an opaque appearance. Such a multilayer film includes a first outer layer comprised substantially of a polymeric material and a central filler-containing polymeric layer substantially continuously joined to one side of the first outer layer. The central filler-containing layer may include about 20 to 60 weight percent fillers relative to the filler-containing layer which are substantially uniformly dispersed therein. A filler such as titanium dioxide or carbonate may be used to give the topsheet a whitish, opaque appearance. The central filler-containing layer has a thickness from about 30 to about 70 percent of the total thickness of the multilayer film. A second outer layer comprised substantially of a polymeric material has one side substantially continuously joined to the second side of the central filler-containing layer. The total multilayer film preferably has at least 20 weight percent filler relative to the total multilayer film. A suitable example of such a multilayer topsheet is found in commonly assigned U.S. Pat. No. 5,261,899, issued Nov. 16, 1993 to Visscher and Perry, which is hereby incorporated herein by reference.

Preferred polymeric materials for the outer layers and the central filler-containing layer include polyolefins, particularly polyethylenes, polypropylenes and copolymers having at least one olefinic constituent. Other materials such as polyesters, nylons, copolymers thereof and combinations of any of the foregoing may also be suitable.

Alternatively, when either a topsheet 22 or a secondary topsheet 25 comprising a fibrous web in accordance with the present invention is utilized, the other member (secondary topsheet 25 or topsheet 22) may be formed of a woven or nonwoven web formed of synthetic fibers (such as polypropylene, polyester, or polyethylene), natural fibers (such as wood, cotton, or rayon), or combinations of natural and synthetic fibers, as well as various paper, tissue, or paper-like fibrous materials. Nonwoven webs may be apertured by techniques known in the art such as needle punching, hydroentangling, ring-rolling, etc. Suitable nonwoven materials can be formed by various processes such as carding, spun-bonding, hydroentangling, and other processes familiar to those knowledgeable in the art of nonwovens. The fibers of the nonwoven material itself may be bonded to one another to provide integrity to the material by any of a number of suitable methods, including heat bonds, pressure bonds, ultrasonic bonds, dynamic mechanical bonds, or any other means known in the art.

Such fibrous materials suitable for use as topsheets or secondary topsheets may either exhibit inherent porosity due to interfiber spacing and/or porosity due to formed apertures extending through the material. Porosity may be provided or enhanced by various mechanical means such as punching, slitting, severing, ringrolling, hydroentangling, or any other suitable method.

The topsheet 22 and secondary topsheet 25, if present, may be bonded to one another by any one of the various bonding methods known in the art. Suitable methods include adhesive bonding such as a uniform continuous layer of adhesive, a patterned layer of adhesive, or an array of separate lines, spirals, or spots of adhesive, or other methods such as heat bonds, pressure bonds, ultrasonic bonds, dynamic mechanical bonds, or any other suitable attachment means or combinations of these attachment means as are known in the art. One suitable bonding method is described in published PCT application WO 93/11725, entitled "Absorbent Article Having Fused Layers", published Jun. 24, 1993 naming Cree et al. as inventors, the disclosure of which is hereby incorporated herein by reference. Representative bonding methods are also described in the above-referenced published PCT application WO 93/09741, entitled "Absorbent Article Having A Nonwoven and Apertured Film Coversheet", published May 27, 1993 naming Aziz et al. as inventors, also hereby incorporated herein by reference. A presently preferred bonding method comprises dynamic mechanical bonding, also known as point thermal bonding. Such a bonding method provides a suitable bond between the layers of the composite topsheet which has sufficient integrity to survive various handling and assembly processes yet does not occlude the apertures in the formed film layer. Particularly when this bonding method is utilized, it is preferred that the materials utilized for the formed film layer and the fibrous layer (first and second topsheet layers, respectively) be thermally similar (i.e., have a similar melting temperature and melting properties).

In a preferred configuration, the secondary topsheet, if utilized, may be smaller in lateral extent in one or more directions than the topsheet while the topsheet and the backsheet will typically generally define the overall size and shape of the absorbent article. The secondary topsheet may therefore be sufficiently smaller than the topsheet so as to be free of the peripheral bond joining the topsheet and the backsheet.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A fluid-previous nonwoven web having a first surface and a second surface, said web comprising:

(a) a hydrophilic nonwoven web, said web comprising a plurality of individual fibers associated with one another to form said web, said fibers having an angular cross section, wherein said web further comprises interfiber capillaries placing said first and second surfaces in fluid communication with one another, said fibers having a first surface energy;

(b) a masking composition, said composition comprising a low surface energy material having a second surface energy less than the surface energy of said fibers of said nonwoven web and a masking agent, wherein said masking composition is randomly distributed in spaced-apart depositions over at least said first surface, creating a surface energy gradient defined by the difference between said first and second surface energies such that said gradient exerts a force on a fluid contacting said first surface to direct said fluid towards and into said capillaries for transporting away from said first surface and in the direction of the second surface.

2. The web of claim 1, wherein said masking agent comprises a material selected from the group consisting of colorants, brighteners, opacifiers, and combinations thereof.

3. The web of claim 1, wherein said agent comprises titanium dioxide.

4. The web of claim 1, wherein said fibers have a delta-shaped cross-section.

5. The web of claim 1, wherein said low surface energy material comprises a curable silicone resin.

6. The web of claim 5 wherein said masking composition comprises titanium oxide dispersed within a molecular structure of said silicone resin.

7. An absorbent article comprising:

(a) a fluid-previous topsheet having a body facing side and a garment facing side;

(b) a fluid-impervious backsheet peripherally joined with said topsheet; and (c) an absorbent core interposed between said topsheet and said backsheet;

wherein said topsheet comprises a fluid previous nonwoven web according to claim 1.

8. The absorbent article of claim 7, wherein said absorbent article comprises a sanitary napkin.

9. The absorbent article of claim 7, further comprising a fluid previous secondary topsheet interposed between said topsheet and said absorbent core.

* * * * *

UNITED STATES PATENT AND TRADEMARK OFFICE
CERTIFICATE OF CORRECTION

PATENT NO. : 6,025,535
DATED : February 15, 2000
INVENTOR(S) : Octavio et al.

It is certified that error appears in the above-identified patent and that said Letters Patent is hereby corrected as shown below:

Title page,
Item [57], ABSTRACT,
Line 1, delete "previous" and insert therefore -- pervious --.

Column 17,
Line 12, delete "previous" and insert therefore -- pervious --.

Column 18,
Line 13, delete "oxide" and insert therefore -- dioxide --.
Line 16, delete "previous" and insert therefore -- pervious --.
Line 22, delete "previous" and insert therefore -- pervious --.
Line 27, delete "previous" and insert therefore -- pervious --.

Signed and Sealed this

Thirteenth Day of August, 2002

Attest:

JAMES E. ROGAN
Attesting Officer  Director of the United States Patent and Trademark Office